(12) United States Patent
Gonzalez et al.

(10) Patent No.: US 10,317,557 B2
(45) Date of Patent: Jun. 11, 2019

(54) METHOD AND DEVICE FOR MEASURING FLUID PROPERTIES USING AN ELECTROMECHANICAL RESONATOR

(71) Applicant: Saudi Arabian Oil Company, Dhahran (SA)

(72) Inventors: Miguel Gonzalez, Houston, TX (US); Max Deffenbaugh, Houston, TX (US); Huseyin Seren, Houston, TX (US); Sebastian Csutak, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 67 days.

(21) Appl. No.: 15/228,241

(22) Filed: Aug. 4, 2016

(65) Prior Publication Data

US 2017/0038491 A1 Feb. 9, 2017

Related U.S. Application Data

(60) Provisional application No. 62/202,512, filed on Aug. 7, 2015.

(51) Int. Cl.
*G01V 1/50* (2006.01)
*E21B 49/08* (2006.01)
(Continued)

(52) U.S. Cl.
CPC .............. *G01V 1/50* (2013.01); *E21B 49/08* (2013.01); *E21B 49/087* (2013.01); *G01N 9/002* (2013.01);
(Continued)

(58) Field of Classification Search
CPC .......... G01N 11/16; G01N 9/002; G01V 1/50; E21B 49/08; E21B 49/087
See application file for complete search history.

(56) References Cited

U.S. PATENT DOCUMENTS 5,837,885 A * 11/1998 Goodbread ............ B82Y 15/00
73/32 A
6,311,549 B1 11/2001 Thundat et al.
(Continued)

FOREIGN PATENT DOCUMENTS

EP 2 246 688 11/2010
EP 2 650 668 10/2013
(Continued)

OTHER PUBLICATIONS

Ochoa, B., et al., "A new sensor for viscosity and fluid density measurement at high temperature and high pressure in a wireline LWD tool", SPWLA 55th Annual Logging Symposium, May 18-22, 2014.
(Continued)

*Primary Examiner* — David Z Huang
(74) *Attorney, Agent, or Firm* — Leason Ellis LLP

(57) ABSTRACT

A method and device are described for making in situ measurements of the density and viscosity of downhole fluids at subterranean wells. An oscillator circuit is deployed in the well comprising an amplifier, a feedback loop, and an electromechanical resonator. The electromechanical resonator is a component in the feedback loop of the oscillator circuit, and has a resonance mode that determines the frequency of the oscillator circuit. The electromechanical resonator is also in contact with the fluid such that the density and viscosity of the fluid influence the resonant frequency and damping of the resonator. The frequency of the oscillator is measured by a microcontroller. In one embodiment, the oscillator circuit periodically stops driving the electromechanical resonator such that the oscillation decays and the rate of decay is also measured by the microcontroller. The density and viscosity of the fluid are determined from the frequency and rate of decay of the oscillation. This measurement technique provides a faster
(Continued)

response time to fluid changes than is possible with conventional measurement methods, and the fast response time opens up new applications for downhole viscosity and density measurements, including determining PVT characteristics, phase diagrams, and flow rates.

16 Claims, 12 Drawing Sheets

(51) Int. Cl.
G01N 9/00 (2006.01)
G01N 11/16 (2006.01)
(52) U.S. Cl.
CPC ........ *G01N 11/16* (2013.01); *E21B 2049/085* (2013.01); *G01N 2009/006* (2013.01)

(56) References Cited

U.S. PATENT DOCUMENTS

| | | | |
|---|---|---|---|
| 6,904,786 B2 | 6/2005 | Matsiev et al. | |
| 6,938,470 B2 | 9/2005 | DiFoggio et al. | |
| 7,562,557 B2 | 7/2009 | Bennett et al. | |
| 8,166,812 B2 | 5/2012 | Desroques et al. | |
| 2002/0178805 A1 | 12/2002 | Difoggio et al. | |
| 2002/0184940 A1 | 12/2002 | Storm, Jr. et al. | |
| 2011/0030455 A1* | 2/2011 | Matsumoto | G01N 11/16 73/54.41 |
| 2011/0036151 A1* | 2/2011 | Andle | G01N 9/002 73/54.41 |
| 2013/0139576 A1 | 6/2013 | Goodbread et al. | |
| 2013/0219997 A1* | 8/2013 | Sullivan | E21B 49/10 73/53.01 |
| 2014/0238668 A1* | 8/2014 | Bittleston | E21B 43/26 166/250.01 |
| 2015/0096385 A1 | 4/2015 | Downie et al. | |
| 2016/0188951 A1* | 6/2016 | Benkley, III | G06K 9/00033 382/124 |
| 2016/0320769 A1 | 11/2016 | Deffenbaugh et al. | |
| 2017/0328201 A1* | 11/2017 | Rodney | E21B 49/08 |

FOREIGN PATENT DOCUMENTS

| | | |
|---|---|---|
| GB | 2 369 887 | 6/2002 |
| GB | 2 421 573 | 6/2006 |
| WO | 0225630 A2 | 3/2002 |
| WO | 2004082363 A2 | 9/2004 |

OTHER PUBLICATIONS

Ochoa, B., et al., "A new sensor for viscosity and fluid density measurement for oil well drilling applications", Sensoren and Messsysteme Jun. 3-4, 2014 in Nurnberg (ISBN 978-3-8007-3622-5).

Mishra, Vinay K., et al., "Downhole viscosity measurement: revealing reservoir fluid complexities and architecture", SPWLA 55$^{th}$ Annual Logging Symposium, May 18-22, 2014.

Toledo, J. et al., "Application of Quartz Tuning Forks and Extensional Microresonators for Viscosity and Density Measurements in Oil/fuel Mixtures" Microsystem Technologies Microsyst Technol 20.4-5: 945-53. Web. Published Online: Feb. 6, 2014.

Freyss, Henri et al., "PVT Analysis for Oil Reservoirs" Reservoir Engineering, The Technical Review, vol. 37 No. 1, pp. 4-15 Published: Jan. 1, 1989.

Examination Report in Corresponding European Patent Application No. 16754041.8 dated Dec. 4, 2018. 6 pages.

* cited by examiner

Cantilever mode

Scissoring mode

Parallel excitation

Orthogonal excitation

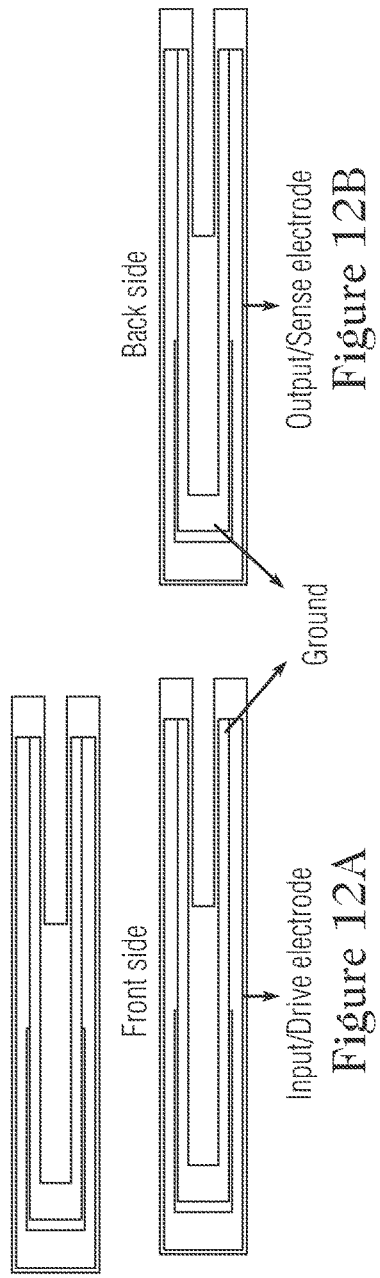
Figure 12A
Figure 12B
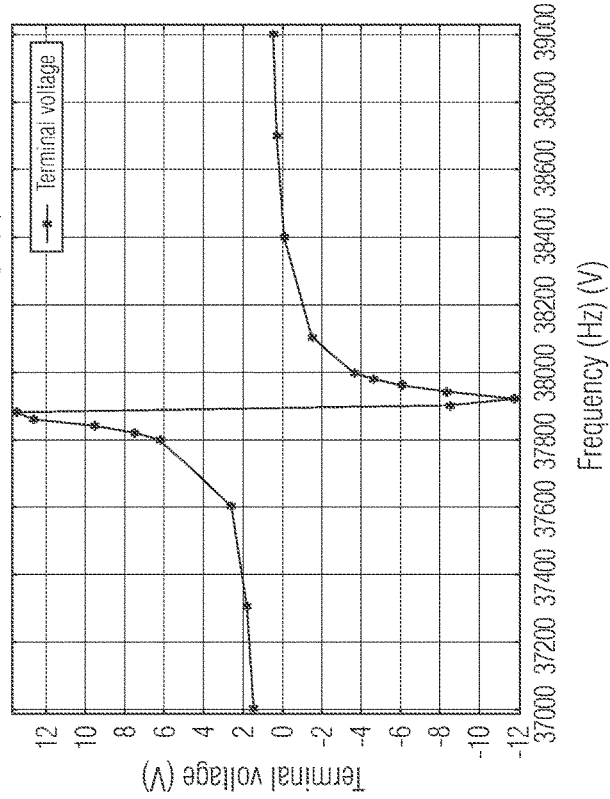
Figure 12C

METHOD AND DEVICE FOR MEASURING FLUID PROPERTIES USING AN ELECTROMECHANICAL RESONATOR

CROSS-REFERENCE TO RELATED APPLICATION

The present invention claims priority to U.S. patent application Ser. No. 62/202,512, filed Aug. 7, 2015, which is hereby incorporated by reference in its entirety.

FIELD OF THE INVENTION

The present invention generally relates to the field of petroleum engineering, and more particularly to a method and device for obtaining in situ measurements at a subterranean well of the viscosity and density of downhole fluids.

BACKGROUND OF THE INVENTION

A multiplicity of hydrocarbons, brines, other liquids and gases and supercritical fluids, slurries, foams and emulsions are produced from, found in, used in the construction of, or injected into subterranean wells. These fluids will be known collectively as downhole fluids. Knowledge of the physical properties of these fluids, such as their density and viscosity, is critical to the drilling, completion, operation, and abandonment of wells. These wells may be used for recovering hydrocarbons from subsurface reservoirs, injecting fluids into subsurface reservoirs, and monitoring the conditions of subsurface reservoirs.

Fluids include matter in its liquid, gaseous, and supercritical states. Downhole fluids include one or more fluids produced from the earth such as hydrocarbons, brines, and other fluids occurring in subsurface reservoirs, as well as fluids such as brines, carbon dioxide, and methane which may be injected into the subsurface to enhance production of hydrocarbons or for disposal purposes. Downhole fluids also include slurries containing liquid and solid components like drilling mud and cement which are used in the construction of wells. One or more downhole fluids may be found simultaneously within a subterranean well, as in a multiphase flow, and they may interact forming emulsions and foams. Downhole fluids will also be understood to include substances which are fluids at reservoir temperature and pressure even if they may be solids at colder temperatures nearer to the surface.

Downhole fluid properties include the viscosity and density of the individual fluid phases as well as the effective viscosity and density of the aggregate fluid consisting of multiple fluid phases. Newtonian fluids are well characterized by a single viscosity. In non-Newtonian fluids, such as slurries, the viscosity may vary with the flow conditions, for example with the stress or shear rate applied to the fluid. Properties of non-Newtonian fluids also include rheological parameters that describe this dependence of viscosity on flow conditions.

Downhole fluid properties are known to vary with temperature and pressure, and the characteristics of this variation is an important property of the downhole fluid. This variation is described, for example, by the PVT (Pressure-Volume-Temperature) characteristics of the fluid which describe how the density varies with pressure and temperature, or by the viscosity variation with pressure and temperature. As pressure and temperature of a fluid changes, the fluid may undergo state changes, for example condensing from a gas to a liquid (e.g., at the dew point), boiling from a liquid to a gas, or transitioning to a supercritical or non-supercritical state. Other types of downhole fluids include structured fluids or dispersions such as emulsions, suspensions and foams, which may undergo structural changes as a function of pressure, temperature, concentration or other chemical or thermodynamic variables. These changes may be detected dynamically as changes in their viscosity and/or density. For instance, one fluid may be dissolved in another and the pressure and temperature conditions under which a fluid becomes dissolved or ceases to be dissolved (e.g., the bubble point) or where solids may precipitate from a fluid is an important property of the fluid. The depth or location in a well where these state changes and this dissolution and precipitation occur is critical information for optimally producing fluids from the well or injecting fluids into the well. Additionally, the density (or API gravity) and viscosity of oil is indicative of its type and value and, as a function of depth, may be used to understand reservoir structure and compartmentalization. Asphaltene content may also be inferred from viscoelastic properties of the produced hydrocarbons. Understanding the PVT characteristics of produced fluids is also important for optimizing surface facilities design, including deciding the optimal pressure for surface separators. State change, dissolution, and precipitation are generally accompanied by a change in viscosity and density of the fluid so that a measurement of viscosity and density as a function of pressure and temperature can identify the temperature and pressure at which these changes occur.

Determining the viscosity and density of fluids in a subsurface reservoir provides important data for optimizing production and reservoir models. Typically, produced fluids are sampled at the surface. Then, in a laboratory, downhole temperature and pressure conditions are applied to the samples and their viscosity, density, and other properties are measured. However, when hydrocarbon liquids from the reservoir are brought to surface temperature and pressure (e.g., as they travel up a well) dissolved gas is released and asphaltenes may precipitate. These changes can be difficult to accurately reverse in the laboratory, so that the viscosity measured in the laboratory may be different from the viscosity that the fluids had in the reservoir, even if the laboratory measurement is made at reservoir temperature and pressure. Furthermore, the process of acquiring samples at a well, transporting them to a laboratory, and making measurements there is costly and time consuming. In addition, the need to transport samples to a lab to acquire fluid properties data prevents these data from being used in real time to respond to changing conditions at the well. Accordingly, there is a need for a sensor that can make an in situ measurement of downhole fluid viscosity and density in downhole or field conditions.

The viscosity and PVT characteristics (or phase diagram) of downhole fluids are typically measured in laboratories and these measurements are used to infer the viscosity and density of the fluid in the reservoir and along the wellbore, and to infer where significant transitions such as state changes, bubble points, and dew points will occur. However, due to the irreversible changes that can occur in fluids as they are brought to the surface as well as uncertainty around exactly where certain conditions of pressure and temperature will be met in the actual well, these inferences may be inaccurate. See Freyss, Henri et al., "PVT Analysis for Oil Reservoirs" RESERVOIR ENGINEERING, The Technical Review, Vol. 37 Number 1, Pages 4-15 Published: Jan. 1, 1989, which is incorporated by reference in its entirety, for a discussion of the viscosity and PVT characteristics of downhole fluids in connection with hydrocarbon recovery. Accordingly, there is a need for a small, fast, and accurate sensor that can measure hydrocarbon viscosity and density along a producing well, as these data combined with temperature, pressure, and depth/location along the well can be used to determine the true locations and conditions where significant transitions occur.

Downhole fluid flows are often two-phase or multi-phase fluid flows, consisting of two or more distinct or immiscible fluids. The flow regime (e.g., slug flow, laminar flow, bubbly flow) depends on the rate of flow of the different phases as well as the viscosity and density of the phases. The flow regime can significantly impact the effectiveness and durability of downhole equipment, such as artificial lift systems. In some flow regimes the flow rates of the different phases may be coupled while in others the flow rates may be uncoupled. Knowing the volume rate of flow of each phase is important for optimizing production and surface facilities, as well as detecting production problems such as water breakthrough. The simplest flow monitoring sensors measure the total flow rate (without distinguishing between the phases) and measure the volume percent of the different phases. The flow rates of the individual phases are determined by multiplying the total flow by the volume percent of each phase. This measurement is only accurate when all phases move at the same velocity. In some flow regimes, the different phases move at different velocities, which can lead to inaccurate measurements. Accordingly there is a need for a small, inexpensive sensor that can measure the instantaneous viscosity and density of the fluid it contacts to aid in the determination of flow regime, the relative abundance of each phase, the shape and size of the flow structures of each phase, and the degree of velocity coupling between fluid phases. Small device size is also necessary due to limited space inside wells particularly in a scenario where permanent or tetherless sensing is desired while not significantly interfering with hydrocarbon production. The invention addresses these and other needs in the art.

SUMMARY OF THE INVENTION

According to one aspect of the present invention, a method and device are disclosed to make in situ determinations of fluid properties at a subterranean well, where, in various embodiments, the fluid properties are measured at or near the depth of a subsurface reservoir penetrated by the well, in the well but above the reservoir depth, at the surface near the well, or in surface facilities connected by pipelines or tubing to the well. The method is performed by deploying an electromechanical resonator such that it is at least partially immersed in the downhole fluids. In one embodiment, the electromechanical resonator might be housed in a chamber and downhole fluids are selectively drawn into the chamber and optionally separated and/or conditioned (chemically or physically) prior to performing the measurement.

The electromechanical resonator is oscillated at its resonance frequency by powering an oscillator circuit which incorporates the resonator as its frequency defining element. The frequency of the oscillation and damping of the oscillation produced by the oscillator circuit is then measured. The frequency and the damping of the electromechanical resonator are related to the viscosity and density of the downhole fluid by employing a processor configured by code to utilize at least one of: (1) theoretical equations relating frequency and damping to fluid viscosity and density; and (2) empirical curve fitting based on calibration measurements of the resonance frequency and damping of the electromechanical resonator in reference fluids having a known viscosity and density.

In a further aspect of the present invention, a method and device are disclosed for determining the PVT characteristics or phase diagram of a downhole fluid, or a dispersed fluid-fluid (emulsion), solid-fluid (suspension), or gas-fluid (foam) system. In one embodiment measurements of density and viscosity are taken as the device occupies different depths in the well, such that the downhole fluid properties can be measured at the differing pressure and temperature encountered at each depth. Based on these measurements at discrete pressure and temperature points, the full PVT characteristics or phase diagram is reconstructed by interpolation. Typically this interpolation is accomplished by selecting from a family of theoretical PVT characteristics the one which most nearly matches the measured properties along the well. Alternatively the family of PVT characteristics may be empirically determined based on PVT characteristics measured in the laboratory on similar fluids; the PVT characteristic which best matches the limited set of data acquired in the well is selected from this family and assumed to describe the fluid at the well.

According to a further aspect of the present invention, a method and device are disclosed for determining properties of a fluid. The method is performed by exposing an oscillator circuit to an uncharacterized fluid. The oscillator circuit used comprises the following: (1) an amplifier (or a logic gate functioning as an amplifier) with an output and an input; (2) a feedback loop between the output and input of the amplifier or logic gate; and (3) an electromechanical tuning fork disposed within the feedback loop such that the resonant frequency of the tuning fork determines the oscillation frequency of the oscillator circuit. The oscillator circuit is then activated so that the tuning fork reaches its resonant frequency in the uncharacterized fluid. The oscillator frequency is measured. Due to the effect of fluid mass loading on the electromechanical resonator, the oscillator frequency is an indication of the density of the fluid—lower frequencies mean the resonator is in a denser fluid while higher frequencies mean that the fluid by the resonator is less dense. The damping of the resonator is also measured. In one embodiment, the damping of the tuning fork in the uncharacterized fluid is determined by causing the oscillator circuit to stop delivering power to sustain the oscillation such that the oscillation decays with time. The envelope, decay time or decay rate of the decaying oscillation is measured to determine the damping. In another embodiment, the feedback circuitry has an automatic gain adjustment that keeps the oscillation at constant amplitude. Energy dissipation, or damping, is determined based on the supplied gain required to maintain this amplitude. Based on the measured damping the viscosity of the fluid is calculated. Less damping means the fluid at the resonator is less viscous, while more or faster damping means the fluid around the resonator is more viscous.

In some embodiments, the uncharacterized fluid is located downhole. In order to determine the properties of the fluid in this embodiment, the oscillator circuit must be disposed downhole. In a further aspect of the present invention, the oscillator circuit is supported by a wireline tool that is capable of making measurements at multiple points in the well. The oscillator circuit may also be supported by an untethered sensor platform that is capable of making measurements at multiple points in the well. In a further embodiment of the present invention, the sensor and the circuitry are permanently deployed downhole, typically as part of a smart completion where a microcontroller and a battery or other power source are used to take measurements.

In a further embodiment of the present invention, a method and device for determining the volume fraction and flow rates for each phase in a multiphase flow are disclosed. The method includes the step of determining the composition of the fluid, wherein the fluid is a multiphase flow.

In a further embodiment, oleophobic or hydrophobic coatings such as pyrelene or fluorinated compounds are used to preferentially measure a particular phase (brine or oil) in a multiphase flow. In one embodiment, an omniphobic coating or super-repellant surface is applied to the electromechanical resonator to reduce the response time in sensing a change in fluid type between hydrocarbons and brine.

In still a further aspect of the invention, an apparatus for determining properties of an uncharacterized fluid, comprises an oscillator circuit comprising an amplifier having an output and an input, a feedback loop between the output and input of an amplifier or a logic gate, and an electromechanical resonator disposed within the feedback loop such that a resonant frequency of the resonator defines the frequency of the oscillator circuit. The apparatus further includes a means for measuring the period (or frequency) of the oscillation, typically using the timer in a microcontroller which has a stable (e.g., crystal oscillator based) time base. The apparatus further includes a means for determining an energy loss parameter related to the rate at which the electromechanical resonator is dissipating energy.

Two examples of said means for determining an energy loss parameter are described without limiting the scope of the invention. In the first example, the apparatus includes a means to enable and prevent the oscillator circuit from driving the electromechanical resonator and a means to determine the decay rate of the oscillation when the resonator is not driven. The decay rate is the required energy loss parameter as it reflects the rate at which energy losses are occurring from the electromechanical resonator. In the second example, the apparatus includes an automatic gain control (AGC) circuit which maintains the oscillation amplitude at a fixed level, and a means to measure the gain control voltage applied to the AGC. An AGC circuit typically has an input, an output, and a gain control voltage input. The output is equal to the input multiplied by a certain gain, and the magnitude of that gain is determined by the gain control voltage input. The gain control input voltage is derived from the amplitude of the oscillation, for example by an envelope detector, such that the gain is increased when the amplitude is too low and the gain is decreased when the amplitude is too high. The gain control voltage at the AGC required to sustain oscillation at a fixed amplitude is measured as the energy loss parameter, as it is a measure of the rate at which energy losses are occurring from the electromechanical resonator.

In one embodiment, the apparatus comprises a microcontroller with code disposed to convert the period of oscillation and energy loss parameter directly to the density and viscosity of the uncharacterized fluid, for example by comparing their values to a set of calibration measurements where the period and energy loss parameter were measured on fluids of known density and viscosity. In another embodiment, the apparatus comprises a microcontroller with code disposed to store or communicate the period of oscillation and energy loss parameter without converting them to density and viscosity. The latter is the preferred embodiment if the conversion can be performed later in software and if any control decisions that must be made based on measured density and viscosity (such as turning on a valve if density or viscosity are too high) can be made based on the surrogate properties of period and energy loss parameter without converting these explicitly to density and viscosity.

BRIEF DESCRIPTION OF THE DRAWING FIGURES

Figure 11A:
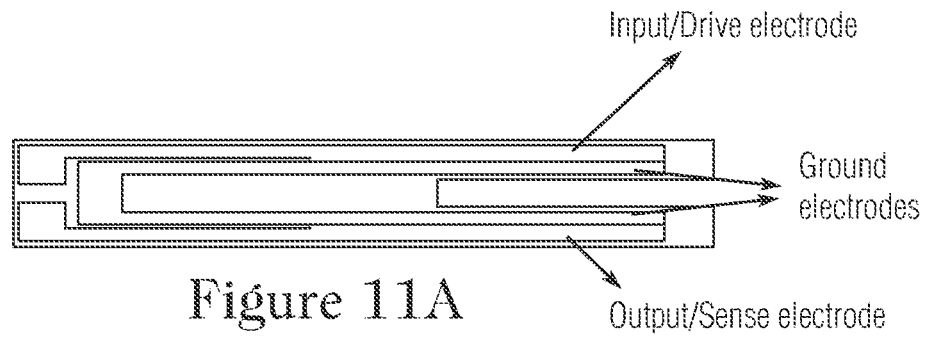
Figure 11B:
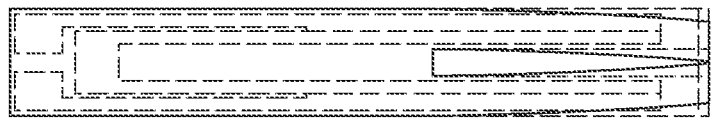
Figure 11C:
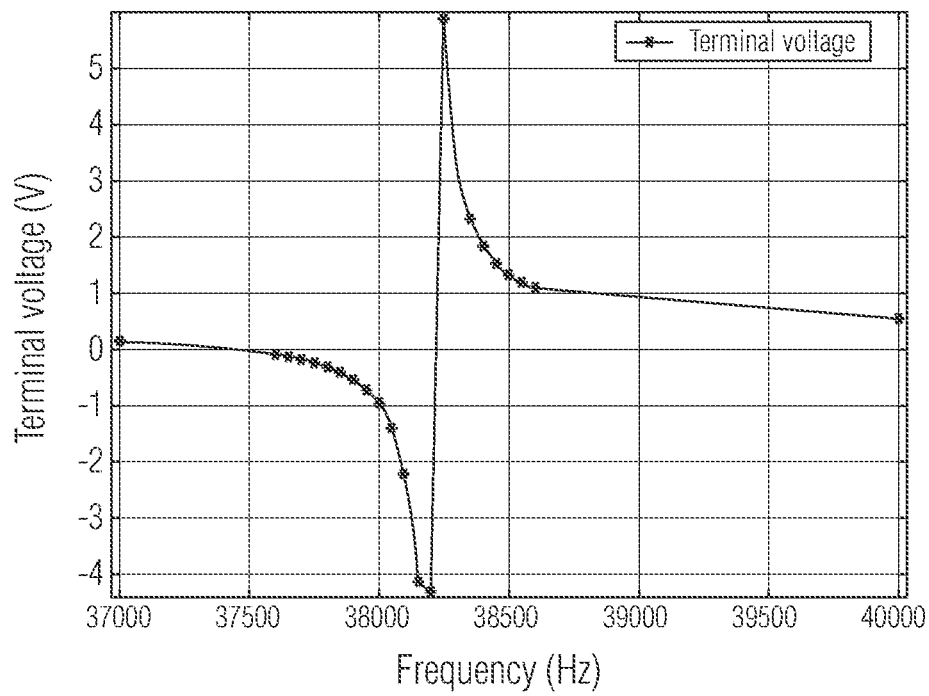
Figure 13:
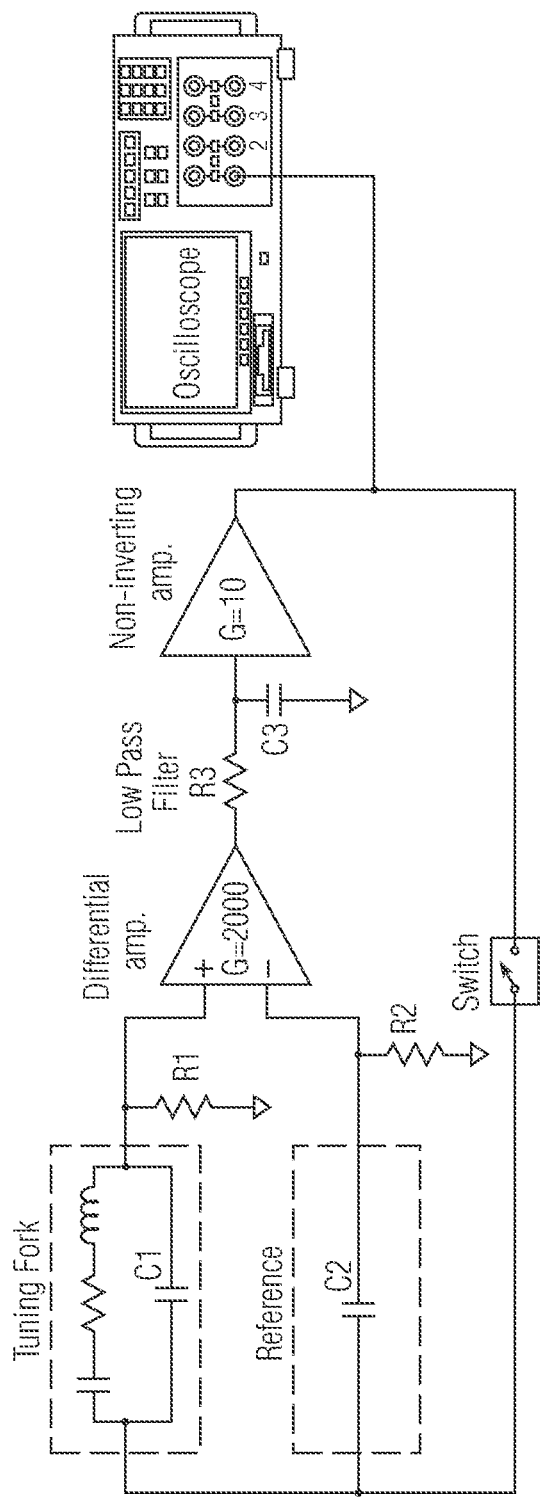

FIGS. 11A-C illustrate a three electrode (INPUT, GROUND, OUTPUT) tuning fork configuration and response for decoupling of drive from sensing signal;

FIGS. 12A-C illustrate a double-sided (back and front) three electrode (INPUT, GROUND, OUTPUT) tuning fork configuration and response for decoupling of drive from sensing signal; and FIG. 13 is a differential electrical circuit diagram with the tuning fork block representing the electromechanical model of the tuning fork with the parasitic capacitance, C1.

DETAILED DESCRIPTION OF CERTAIN EMBODIMENTS OF THE INVENTION

According to a broad aspect of the present invention, the inventors recognized that a small, fast, and accurate sensor capable of measuring viscosity and density and mounted on a platform which enabled it to obtain measurements at various depths along a producing well can, for example, be used to 1) map the PVT characteristics of downhole fluids and identify the locations where the dew point, bubble point, and/or other important state changes and transitions in the fluid properties occur along the wellbore, 2) map the PVT characteristics of a dispersed fluid-fluid (emulsion), solid-fluid (suspension), gas-fluid (foam) system through rapid measurement of changes in density and viscosity 3) determine more accurately the true viscosity and density of the reservoir fluids at reservoir conditions, and 4) determine separate phase densities and viscosities and a time series of the instantaneous phase present at the sensor in a multiphase flow, from which the flow regime, the shapes and sizes of the flow structures of each phase, and the volume flow rates of each phase could be more accurately inferred.

In accordance with one embodiment of the invention, the device comprises a platform for positioning the sensor at a desired depth in an subterranean well, an electromechanical resonator, an oscillator circuit which incorporates the electromechanical resonator as its frequency-defining element, and a microcontroller which measures the frequency (or period) of oscillation of the oscillator circuit and measures the damping of the oscillation. Such an embodiment is a departure from prior art approaches in that the electromechanical resonator defines the resonant frequency of the oscillator circuit, as opposed to conventional arrangements which have an oscillator circuit which is distinct from the resonator and must be tuned until the resonance frequency of the electromechanical resonator is found. The embodiment is also different in that the damping of the oscillation or other energy loss parameter is measured directly to determine the energy losses or damping caused by the fluid contacting the resonator.

An oscillator circuit typically comprises an amplifier with at least one feedback path from the output of the amplifier to an input of the amplifier. A frequency defining element (such as a quartz crystal) is typically included along one such feedback path in such a way as to cause a sustained oscillation at the resonance frequency of the frequency-defining element. This sustained oscillation is produced when the total phase shift around the loop including the frequency defining element and the amplifier is 360 degrees or a multiple thereof and the gain around the loop including the frequency defining element and the amplifier is no less than 1.

The inventors recognized that the circuit arrangement of including the electromechanical resonator within an oscillator circuit as the primary element which determines the frequency of the oscillation offers substantial benefits over prior art methods, including, first, that it is not necessary to search multiple frequencies to find the resonant frequency of the resonator as the oscillator circuit begins oscillation at the required resonant frequency. This makes the measurement using the inventive method much faster than with conventional methods. Second, the total amount and complexity of circuitry required to accomplish the measurement is greatly reduced. Third, a precision oscillator capable of producing accurately controlled frequencies with fine frequency resolution is not required; the inventive circuit simply oscillates at the desired frequency, and this frequency can be measured with a simple crystal-based timer, a device already available on many small microcontrollers. Fourth, incorporating the resonator into the oscillator circuit as the frequency-defining element means that significant energy becomes stored in the resonator, which provides a strong signal for measuring the damping due to the surrounding fluid. By contrast, driving the resonator with an impulse or step function to observe its resonance frequency and damping produces a much smaller signal as only a small fraction of the energy in the impulse or step function would be within the resonant frequency band of the resonator. Fifth, among other benefits, incorporating the resonator into the feedback loop of an amplifier in the oscillator circuit provides an opportunity with efficient circuit design to utilize the same amplifier to provide amplification of the sensor signal during the damping measurement.

Figure 1:
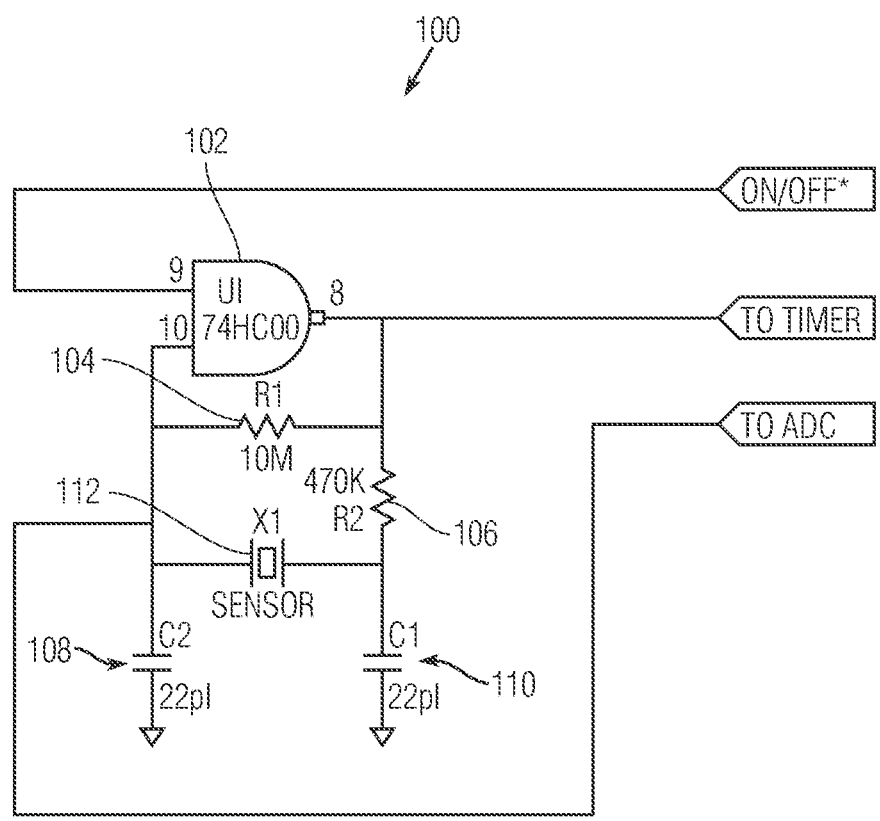
FIG. 1 illustrates an oscillator circuit according to a first arrangement.

There are various ways that the damping can be measured. In one embodiment, the damping is determined by briefly ceasing to electrically drive the resonator so that the oscillation decays in amplitude and the rate of the amplitude decay can be measured. For instance, this can be achieved using a NAND-gate based oscillator circuit, as shown in FIG. 1 and described in more detail below. An envelope detector circuitry can be employed to provide the oscillation amplitude which can then be digitized and fit to an exponential decay curve to determine the damping coefficient. Alternatively, two voltage comparators and a timer can be used to determine how long it takes the envelope to decay between to reference voltage levels and this time can be used to determine the damping coefficient. Alternatively, constant oscillation amplitude can be maintained by using an automatic gain adjustment circuitry that sets the gain of the previously mentioned amplifier in the closed loop. In this alternative measurement technique, there is no need to stop the oscillation to measure the decay time; instead, the amount of gain needed to sustain the constant amplitude can be used to determine the damping coefficient due to the fluid surrounding the electromechanical resonator. The gain of the automatic gain control amplifier can be determined by digitizing the gain adjustment signal which controls its gain and using a prior calibration measurement relating the gain adjustment signal to the amount of gain that the amplifier produces.

According to one embodiment, the sensor can comprise an electromechanical device, which is in contact with the fluid, and which is a component of the circuit which drives and detects the oscillatory motion of the device, as a function of time, as the sensor interacts with the fluid. The motion of the electromechanical device is influenced by the fluid and a quantitative relation is established directly between the fluid viscosity and density and the resonant frequency and damping of the electromechanical resonator. Alternatively, if the fluid viscosity and density are well known functions of temperature and pressure (as for example with methane), a direct relation between frequency and damping can be established with the temperature and pressure of the fluid, allowing real-time knowledge of its thermodynamic state and other properties related to this state (bubble-point, dew-point, GOR, etc.).

Figure 7:
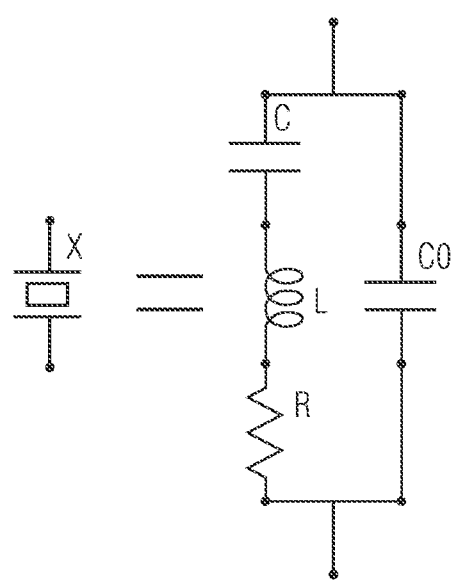
FIG. 7 illustrates the Butterworth-Van Dyke model for piezoelectric resonators.

In particular, a piezoelectric tuning fork can be used as the electromechanical oscillating device. One example of a suitable piezoelectric tuning fork is described in U.S. Pat. No. 7,562,557 to Bennett, et al., which is hereby incorporated by reference in its entirety. However, the invention is not limited to a particular resonator element as long as it can be integrated into an oscillator circuit as part of the oscillator itself. The mechanical properties of the fork, which is a two terminal device, can be described by the Butterworth-Van Dyke model (shown in FIG. 7) as a series resistance (R), inductance (L) and capacitance (C) circuit (RLC circuit) representing, respectively, the mechanical damping, mass, and compliance of the device, with a parallel capacitance (C0) which represents the electrical capacitance of the device including the capacitance between the electrodes of the device, including any stray capacitance between the electrical leads and capacitance due to the dielectric medium surrounding the device. This model represents a resonant system and establishes a direct relation between the mechanical and the electrical domain through the piezoelectric action. When C0 is much larger than C, it becomes difficult to make a highly damped resonator (such as a resonator in a viscous liquid) oscillate. Accordingly, the preferred resonator design utilizes a choice of piezoelectric material, shape, and dimensions to minimize C0 relative to C. The preferred resonator also maintains a high Q factor (quality factor) of the resonance when in liquids, for example, by having reduced contact area with the liquid. Additionally, an inductor (or a circuit which simulates the action of an inductor) can be placed in parallel or series with the resonator to cancel the action of C0 near the resonant frequency, thus making it easier for the oscillator circuit to resonate when the fork is in a highly viscous liquid. Alternatively, a reference capacitor that has an identical or very similar capacitance with the piezoelectric oscillator's parasitic capacitance can be used in a differential measurement scheme (FIG. 13). In this technique identical input signals are fed to the piezoelectric resonator and the reference capacitor, and their outputs are subtracted from each other to cancel out the parasitic capacitance contribution. Even when the electromechanical response signal is very small compared to the parasitic signal, subtraction and amplification can enable oscillation even in a high damping environment. A differential amplifier can be used for subtraction. In one embodiment, the reference capacitor can be a second tuning fork with its forks clamped or held by epoxy. This ensures that there is no major contribution from the piezoelectric (electromechanical) response of the reference capacitor around the frequencies of interest but only from the parasitic capacitance. A near identical capacitor can be made by patterning electrodes on the same type of piezoelectric substrate with the same geometry as the electromechanical resonator that does not have the tuning fork shape; thus, it does not possess any resonance frequency around the tuning fork's resonance frequency.

In another embodiment, driving and sensing functions of the electromechanical resonator can be decoupled. This can be done using different physical effects for driving and sensing such as using various combinations of transductions between electrical, magnetic, mechanical and optical domains. Or, if the same transduction method is used for driving and sensing, decoupling can be also done by spatially separating the regions of driving and sensing. Depending on the used transduction the necessary separation length may differ. In the specific example of piezoelectric tuning fork, it can be driven to its resonance by several means and resulting mechanical deformation on the piezo material can be sensed as a voltage output via the patterned electrodes. This method minimizes the parasitic capacitance and direct electrical signal coupling of the input signal to the output. In the simplest form, the tuning fork can be rigidly mounted on a mechanical shaker, such as a shearing piezo transducer. Applying an electric signal to the shearing piezo at the resonance frequency of the tuning fork, the motion of the shearing piezo can be mechanically coupled to the tuning fork and the tuning fork's resonance mode can be excited. As the tuning fork deforms, it produces a spatial charge distribution along its piezoelectric crystal which can be picked up as a voltage difference between the patterned electrodes on the tuning fork. The coupling efficiency of the initial motion to the desired resonance frequency depends on the orientation of the tuning fork with respect to the direction of motion of the shearing piezo and the stiffness of the bonding between the two bodies. For example, to excite the scissoring mode of the tuning fork without exciting the fundamental cantilever mode of the whole tuning fork body, shearing motion direction should be orthogonal to the scissoring motion direction as shown in FIGS. 10A-D. Alternatively, the electrodes can be patterned on the tuning fork so that driving and sensing can be performed by far electrodes as in FIGS. 11A-C. In this three electrode scheme, the parasitic capacitance between input and output ports can be several orders of magnitudes smaller than the parasitic capacitance of a two terminal device with a similar geometry. By comprising the fabrication complexity, a second set of electrodes can be patterned on the back side of the tuning fork. The front face electrodes can be used for driving and the back side electrodes can be used for sensing. In this case the electromechanical conversion efficiencies can be further increased as shown in FIGS. 12A-C.

According to one aspect of the operation of such a circuit, the resonator is incorporated into an oscillator circuit, which is then turned on. The oscillator circuit can include the circuits of FIGS. 1 and 3, which are described in more detail below. Through a continuous feedback mechanism from the circuit, the tuning fork starts its oscillation from small fluctuations in its motion that overcome the damping from the environment and grow until a maximum amplitude is reached. At this point, the feedback mechanism is switched off and the oscillation of the resonator decays due to the environmental damping. The process is repeated continuously and the frequency and decay time of oscillation is obtained at each switching cycle.

The model that describes the oscillation decay is that of a damped un-driven harmonic oscillator, whose solution for the velocity of oscillation (proportional to the current generated by the piezoelectric effect) is given by:

$$v(t)=Ae^{-t/\tau}\cos(\omega t+\varphi),$$

where $\varphi$ is the phase of oscillation, the decay time constant, $\tau$, is related to the damping by the fluid, and the frequency, $\omega$, is related to the effective mass of the resonator including the added mass of fluid dragged by the resonator. These quantities are related to the quality factor, Q, of the oscillator by $$\tau = \frac{2Q}{\omega_0}$$

and $$\omega=\omega_0\sqrt{1-\tfrac{1}{4}Q^2},$$

In a liquid environment, Q becomes very small, say, of order 10. Using the equation above, and for an estimated natural frequency, $\omega_0$, in the tens of kilohertz, say, $3\times10^4$ KHz, it can be appreciated that a time constant of approximately one millisecond is obtained, allowing for a very quick measurement and "real-time" information of the properties of the fluid to be calculated and reported to downstream systems, such as hardware-processor based machines that execute or otherwise implement code to configure those machines to process the fluid characteristics data received from such a circuit within a producing well.

Figure 9:
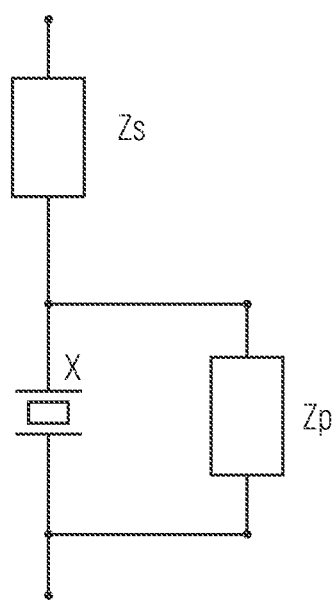
FIG. 9 shows the addition of parallel and series electrical impedances to the resonator as can be required to enable the inventive circuit to oscillate when the resonator is in liquids or otherwise has large damping.
Figure 10A:
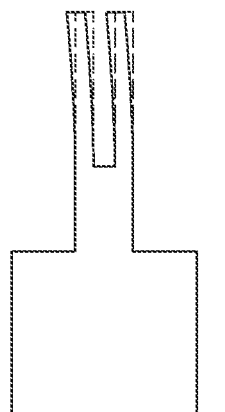
FIGS. 10A and 10B illustrate two of the vibrational modes of a tuning fork oscillator and FIGS. 10C and 10D illustrate tuning fork response under in-plane shear actuation with external piezoelectric transducer with the arrows pointing in direction of actuation.
Figure 10B:
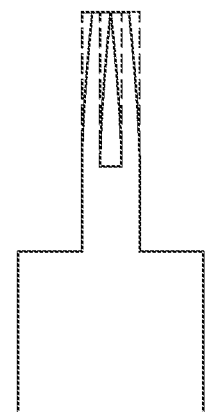
Figure 10C:
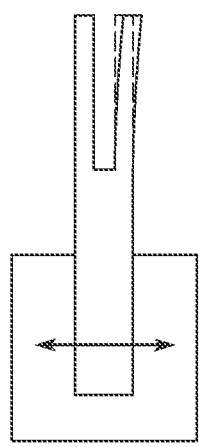
Figure 10D:
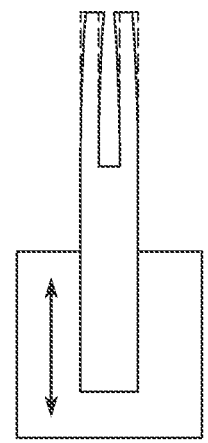

Various oscillator circuits can be adapted to work with the electromechanical resonator sensor. The oscillator circuit must be able to oscillate for all environments in which measurements are to be obtained. For liquid environments, the Q (i.e., quality factor) of the resonator is small (e.g., on the order of 10), and some oscillator circuits may not provide enough amplification to sustain an oscillation. In such cases, additional amplification can be employed. For example, if an unbuffered logic gate is not able to provide sufficient amplification to sustain oscillation in lossy environments, it can be replaced with a buffered logic gate or with multiple logic gates in series to provide the additional amplification required for oscillation. In some cases, when the Q factor of the resonator is small due to being in a viscous fluid, it may not produce sufficient phase shift to cause an oscillator circuit to oscillate. In this case, an additional impedance such as a reactance can be added in parallel and/or in series with the resonator to provide the additional phase shift. As shown in FIG. 9, an impedance Zp is added in parallel with the resonator X, and an impedance Zs is added in series with the resonator X. It will be understood that the "SENSOR" shown by the crystal schematic symbol in FIG. 1 and FIG. 3 includes both the electromechanical resonator and the parallel and/or series impedance that must be added to the resonator to cause the circuit to oscillate in the fluids of interest. Persons skilled in the art will recognize that the impedance can be added as networks of one or more resistors, capacitors, and inductors or as active circuits which emulate the current-voltage relationships of these networks. Active circuits have certain advantages as they can create current-voltage relationships which cannot be created by passive components such as a "negative resistor." Small active circuits can also emulate relationships where the corresponding passive component would be much larger, such as when emulating a large inductor. In one embodiment, in the circuit shown in FIG. 1, the "SENSOR" consists of an inductor in series with the resonator to enable the circuit to operate in fluids with higher viscosities.

In one embodiment, an oscillator circuit suitable for use in connection with the present invention includes a means to cause it to stop driving the electromechanical resonator so that the decay of the oscillation can be observed. For instance, the feedback loop containing the electromechanical device can be opened, or other circuit components in the oscillator circuit opened, shorted, or otherwise changed so that the resonator changes from a driven state to an undriven state. The circuitry of the oscillator circuit, or separate circuitry, can include a means to measure the frequency of oscillation and a means to measure the decay rate of the oscillation. Two such embodiments are discussed below.

Referring to FIG. 1, a circuit 100 includes a NAND logic gate 102 configured, as described below, as an amplifier, resistors 104 and 106, and capacitors 108 and 110 connected around a "sensor" 112 which comprises an electromechanical resonator that both forms a part of the oscillator circuit in order to define the oscillation of the circuit and which is configured to be in direct contact with a fluid to be measured, such that the effect of the fluid on the behavior of the resonator can be measured to determine characteristics of the fluid. The gain in the oscillator circuit 100 is provided by the NAND logic gate (U1) 102, that is, the NAND/logic gate functions as an amplifier for the circuit. The oscillator is disabled by a logical low level on the ON/OFF* input and enabled by a logical high level on the ON/OFF* input. This input can be supplied by a digital output from a microcontroller, for example, to control whether the oscillator circuit is in a driven or undriven mode. After oscillation, the undriven mode is suitable for gathering damping data and determining fluid characteristics, such as using the formulas noted above or other equations that benefit from the damping data. The "TO TIMER" output of the circuit has a square wave at the frequency of oscillation. This output can be provided, for example, to a timer input of the microcontroller so that the frequency of the oscillation can be accurately measured by the timer system of the microcontroller. The "TO ADC" output of the circuit can be provided to an analog-to-digital converter to sample the decaying oscillation and determine the damping, if desired.

Figure 2:
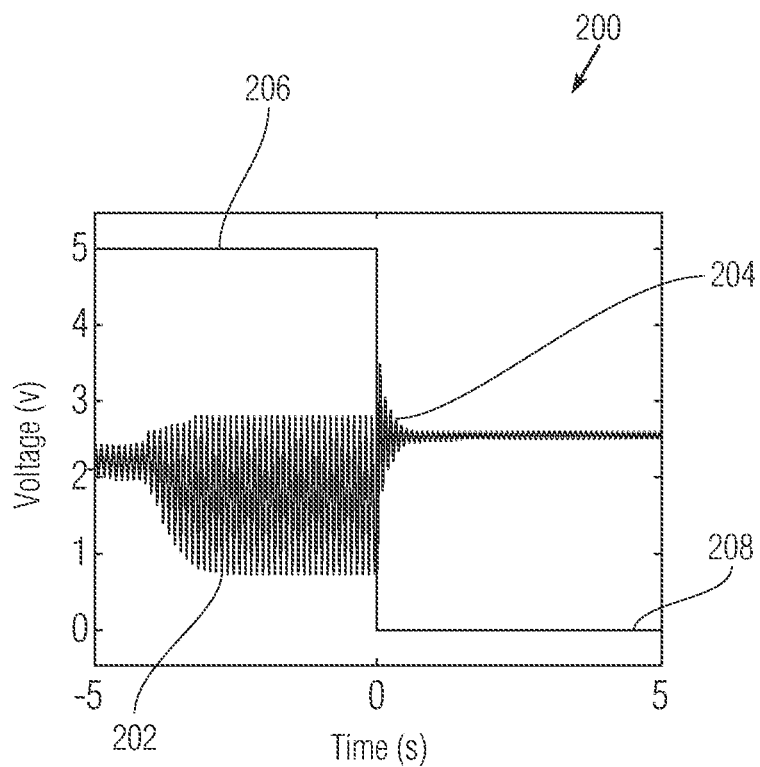
FIG. 2 illustrates electrical waveforms recorded within an oscillator of the first arrangement.

FIG. 2 shows an output graph 200 that includes two waveforms 202 and 204 from the circuit 100. When the ON/OFF* input is high 206, the oscillation begins, eventually reaching a stable amplitude as can be seen in waveform 202. Then when the ON/OFF* input goes low 208 (at time=0 seconds in the diagram of FIG. 2), the NAND gate is disabled, and the oscillation decays, as shown in the waveform 204. The waveform at TO ADC output is shown at 202, 204. These data illustrated in FIG. 2 were Measured with the Sensor in Vacuum. The time to begin oscillation and the decay times are much faster when the sensor is in liquid. In any event, the damping rate of the electromechanical device in a reference liquid, and at a prescribed temperature and pressure, can be obtained for benchmarking purposes, such as to calibrate a given sensor 112.

Figure 3:
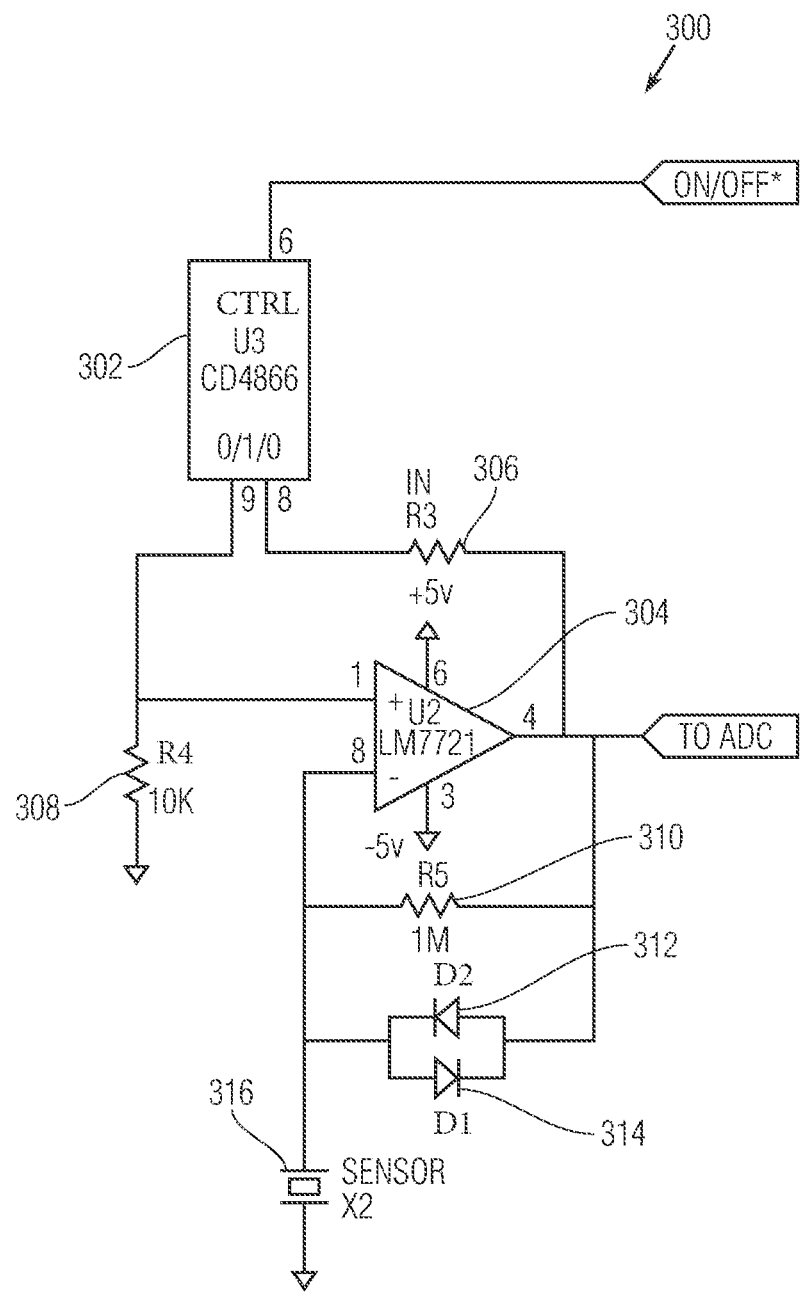
FIG. 3 illustrates an oscillator circuit according to a second arrangement.

FIG. 3 shows another embodiment in which circuit 300 is provided. The circuit 300 includes an analog switch 302, an operational amplifier 304, resistors 306, 308, and 310, and diodes 312 and 314. Again, in salient part, the circuit 300 includes a "sensor" 316 which comprises an electromechanical resonator both forms a part of the oscillator circuit in order to define the oscillation frequency of the circuit and which is configured to be in direct contact with a fluid to be measured, such that the effect of the fluid on the behavior of the resonator can be measured to determine characteristics of the fluid. The gain in the oscillator circuit 300 is provided by the operational amplifier (op amp) (U2) 304. When there is a logical low level at the ON/OFF* input, the analog switch U3 302 is open and the oscillation is not driven (i.e. it decays). In this mode, the op amp 304 functions as a current-to-voltage converter, providing a voltage on the TO ADC output that is proportional to the decaying current oscillation from the sensor. When there is a logical high level on the ON/OFF* input, the analog switch U3 302 is closed allowing positive feedback which causes a sustained oscillation at the resonant frequency of the sensor. The ON/OFF* input can be supplied by a digital output from a microcontroller. The "TO ADC" output of the circuit can be provided to an analog-to-digital converter which samples the sustained and decaying oscillations and enables a processor to determine the frequency of oscillation and the decay time. Diodes 312 and 314 (D1 and D2) prevent the op amp output from being driven into saturation. Without these diodes, there would be a reduction in oscillation frequency due to the time it takes the op amp to come out of saturation.

In another embodiment, the damping is determined based on the amount of negative resistance which must be added in series or parallel with the resonator to sustain the oscillation at constant amplitude (e.g., the circuit of FIG. 3 can be modified to accomplish this operation, where the resistor (308)—which defines the negative resistance—is replaced by a variable resistance device, such as an N-channel enhancement mode MOSFET, and the gate voltage of the MOSFET (which determines the drain-source resistance in the linear region of operation) is adjusted to keep the amplitude of the amplifier output constant. FIG. 3 thus shows a circuit of an oscillator using an operational amplifier. The resistance which the MOSFET is supplying, and, therefore, the negative resistance required to keep the oscillation amplitude constant, can be determined by sampling the gate voltage on the MOSFET). In another embodiment, the damping is determined based on the amount of power that must be added to the resonator to sustain the oscillation at constant amplitude. In another embodiment, the damping is determined based on the amount of gain that must be applied in the feedback loop containing the resonator within the oscillator circuit to sustain the oscillation at constant amplitude.

Suitable platforms that can deliver a sensor to a desired location or set of locations in a producing well include wireline tools, as are known to persons skilled in the art, untethered sensors, as described in co-pending U.S. patent application Ser. No. 15/143,128, filed on Apr. 29, 2016, entitled METHOD AND DEVICE FOR OBTAINING MEASUREMENTS OF DOWNHOLE PROPERTIES IN A SUBTERRANEAN WELL, which is hereby incorporated by reference as if set forth in its entirety herein, or on network nodes at different depths in a permanently deployed network of sensors disposed within the well. The structure of the device makes it particularly useful for remote, downhole operations as the device can be made to fit into a small package (e.g., resonator and circuit can fit in less than 1 cc volume), and consume little power (e.g., approximately 1 micro Joule per measurement).

Figure 8:
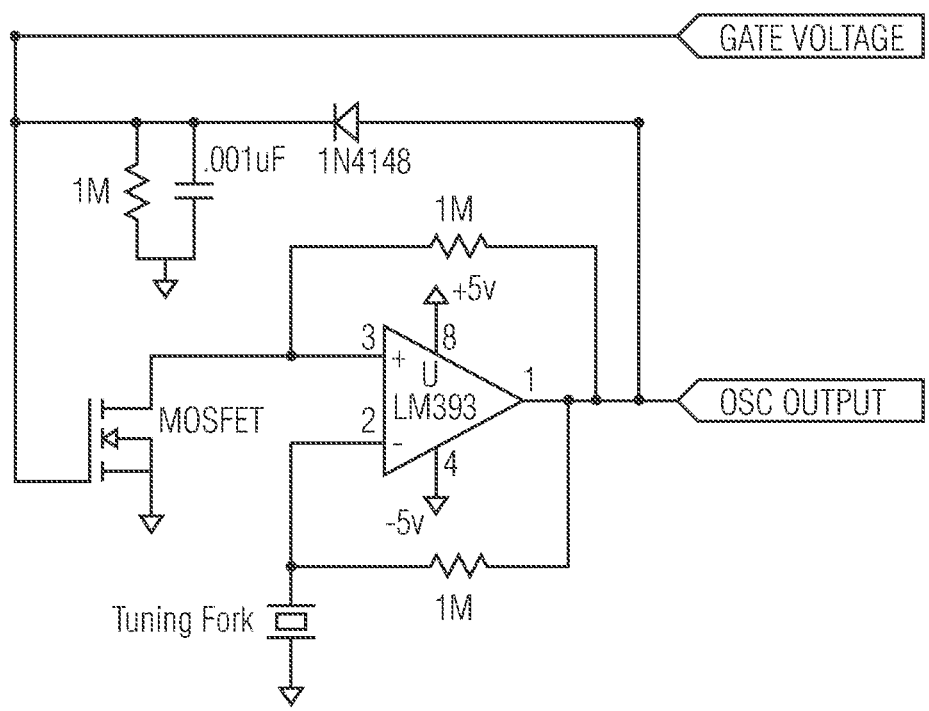
FIG. 8 illustrates an oscillator circuit where a variable negative resistance is simulated and controlled in a feedback loop to maintain a constant oscillation amplitude.

In one embodiment, the circuit of FIG. 3 is modified as shown in FIG. 8 to implement automatic gain control. The resistor (308 in FIG. 3) which sets the negative resistance seen at the non-inverting input of the operational amplifier can be replaced by an N-type enhancement mode MOSFET, in which the gate voltage supplied to the MOSFET is the gain control voltage and is the output of an envelope detector applied to the oscillation at the operational amplifier output. Thus, the MOSFET gate gets a voltage that depends on the amplitude of the oscillation. If the amplitude of the oscillation decreases, the gate voltage will decrease. This will increase the drain-to-source resistance of the MOSFET increasing the negative resistance added to the resonator and increasing the amplitude of the oscillation. If the amplitude of the oscillation increases, the gate voltage will increase. This will decrease the drain-to-source resistance of the MOSFET, decreasing the negative resistance added to the resonator and decreasing the amplitude of the oscillation. Thus, the amplitude of the oscillation will be maintained at a constant level using a circuit of such an arrangement. The negative resistance required to maintain the constant amplitude oscillation can be determined by measuring the gate voltage applied to the MOSFET combined with a calibration curve that gives the drain-source resistance of the MOSFET as a function of its gate voltage. In this regard, a hardware processor can execute or otherwise implement code therein to identify resistance from a calibration curve (or a function that represents the calibration curve), based on the measured gate voltage.

In one embodiment, the circuit alternatively can be configured to drive the resonator such that the oscillation is initially established and at least briefly sustained, and then ceases to drive the resonator such that the oscillation is permitted to decay (e.g., using the circuit of FIG. 1, for example) so that a decay measurement can be taken or otherwise completed. In another embodiment, the gain of the circuit is adjusted to maintain a constant amplitude of oscillation and the amount of gain required is measured as an indicator of the amount of damping. This is because greater damping requires greater gain to sustain a constant oscillation. In another embodiment, a circuit is configured to simulate a "negative resistor" connected to the resonator. The amount of negative resistance is adjusted automatically to maintain a constant amplitude oscillation, and the amount of negative resistance required is measured as an indicator of the damping. This can be employed because a greater negative resistance is required to offset a greater damping energy loss which can be thought of as a (positive) resistor internal to the resonator.

In one embodiment the variable resistor circuit can be as shown in FIG. 8, in which the adjustable resistor is actually the drain-source resistance $R_{DS}$ of a MOSFET, which is adjusted by the gate voltage of the MOSFET. The gate voltage of the MOSFET in this embodiment is generated by an envelope detector on the amplifier output, so that a larger amplitude output results in a larger gate-source voltage and therefore a smaller $R_{DS}$ which causes the oscillation amplitude to decrease until a $R_{DS}$ becomes exactly right to offset the damping in the resonator. The gate voltage is sampled by an A/D converter in the microcontroller which can be related to the value of $R_{DS}$ and therefore the amount of damping in the resonator, for instance, using code executing within the microcontroller which relate the values just described. The frequency of the oscillation can also be measured by the microcontroller. From this measurement and the value of $R_{DS}$, the frequency which the undriven decaying oscillation has can be calculated.

In one embodiment, a system and method is provided that can also measure temperature and pressure in addition to density and viscosity of all fluids present in a multiplicity of locations along a well bore. The temperature and pressure measurements are implemented by including temperature (for example RTD) sensors and pressure transducers that are commercially available. Their readings are measured by an analog-to-digital converter that interfaces to the microcontroller in the device such that temperature and pressure data can be recorded or transmitted along with density and viscosity.

Although viscosity is not plotted in PVT diagrams, it can be used as an indicator of when a particular state change, bubble point, dew point, etc. has occurred. An untethered sensor ball (such as the one described in the co-pending U.S. patent application Ser. No. 15/143,128, referenced above, for example) provides an inexpensive solution for measuring fluid properties at all pressures and temperatures between the surface and any given reservoir depth. By measuring temperature, pressure, and the density and viscosity of all fluid phases that are encountered while traveling down the well from the surface to the selected reservoir depth, the device, methods and system of the present invention can reconstruct the viscosity and phase diagram information for the produced fluids along the most important pressure—temperature trajectory, i.e., that found in the wellbore.

It is recognized that knowing the viscosity and density of each phase could help to determine flow regime and improve the accuracy of phase flow rates. The ability to measure viscosity and density at a rapid sampling rate reveals, instantaneously, which phase is present in a multiphase flow, providing a time series of the phase at the sensor location. This time series can be used to determine the abundance of each phase as well as the size and shape of the flow structures of each phase and thus the flow regime. A second such time series downstream of the first can be correlated with the first to determine how long it took individual packages of fluid to move between the sensors, providing a more accurate measurement of phase flow rates.

As discussed above, the oscillator circuit incorporates an electromechanical resonator disposed within the feedback loop of the circuit such that the resonant frequency of the resonator defines the oscillation frequency of the oscillator circuit. In addition to defining the oscillation frequency of the circuit, the resonator also contacts the fluid to be measured. This arrangement allows the resonant frequency to be determined much faster as compared to other systems in which the resonator is separate and distinct from the oscillator circuit that drives it. Accordingly, the arrangement disclosed herein allows for increased speed of measurement. The increased speed of measurement is beneficial in many respects. For example, in a producing well there are often multiple fluids entering the well. The increased speed of measurement results in an increased number of measurements which allows one to distinguish between multiple fluid types in a producing well and determine correct viscosity for each fluid type. In contrast, systems that have slower measurements provide less accurate results as the sensor can be in more than one fluid type during the time of the measurement.

In addition, the increased speed of the system and method described herein allows one to resolve separate fluids in a multiphase flow in a producing well. In contrast, slower sensors will blur fluid properties over the various fluids they encounter during the measurement time. The increased speed of the sensing allows for the determination of composition and structure of multiphase flows. Again, the increased speed of the sensor allows for multiple, fast measurements that allow one to sense and perceive separate fluid phases in the downhole fluid while other sensors don't respond fast enough to provide the necessary granularity in the data to perceive the separate fluid phases. In a producing well, the sensor can be in a different fluid type every few milliseconds as bubbles of oil, gas and brine rush past.

Figure 4:
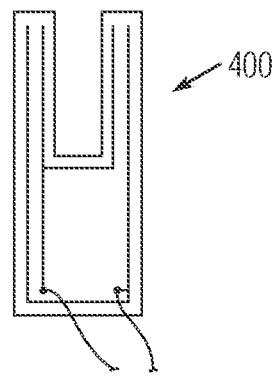
FIG. 4 illustrates a tuning fork resonator.
Figure 5:
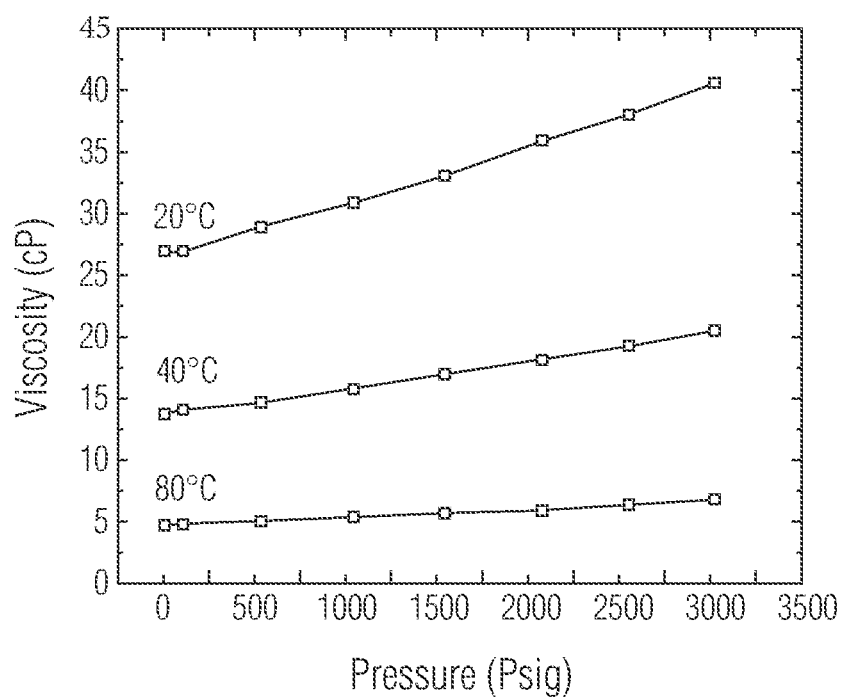
FIG. 5 illustrates an example of measured viscosity data.
Figure 6:
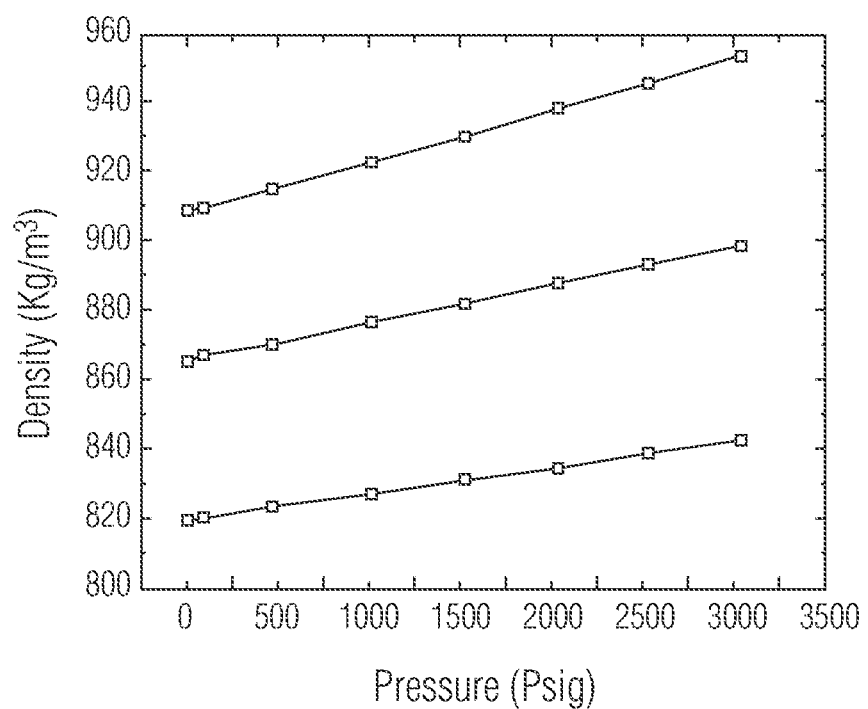
FIG. 6 illustrates an example of measured density data.

According to one, non-limiting example, one embodiment was tested under laboratory conditions. Referring to FIG. 4, the system includes a tuning fork 400 as the electromechanical resonator (i.e., a wired tuning fork oscillator). A full characterization of the tuning fork was performed under simulated downhole conditions of pressure and temperature. The device was actuated and sensed piezo electrically using a lock-in amplification technique as well as a direct frequency response measurement of its impedance. Resonance peaks were obtained and fitted with the peak width, amplitude and resonance frequency as fitting parameters. Peak width and frequency allow for the extraction of the damping and added mass of the oscillator in the fluid. A hydrodynamic model was developed to calibrate the resonance response with the viscosity and density of a test fluid. For this purpose, the sensor was activated in different fluids (air, water, mineral oil, hydraulic oil) and the calibration parameters were obtained. The device was later tested at different conditions of pressure and temperature to simulate downhole conditions (see FIG. 5 and FIG. 6). More specifically, FIG. 5 shows the results for the measured viscosity of ISO 15 hydraulic oil at high pressures and high temperatures and FIG. 6 shows the results for the measured density of ISO 15 hydraulic oil at high pressures and high temperatures.

The device was found to be appropriate for measuring viscosity in the ranges of interest (up to 50 cP).

Based on the foregoing, it should be understood that the invention can be realized in a number of ways, at differing levels of specificity, as can be gleaned from the following points.

According to one point, a method for making an in situ determination of fluid properties at a location of interest is provided, which includes the steps of:
  a. deploying an electromechanical resonator at a subterranean well such that the electromechanical resonator is at least partially immersed in the downhole fluids at the location of interest;
  b. causing the electromechanical resonator to oscillate at its resonance frequency by powering an oscillator circuit which incorporates the resonator as its frequency defining element;
  c. measuring the frequency of the oscillation produced by the oscillator circuit;
  d. measuring the damping of the oscillation produced by the oscillator circuit; and
  e. relating the frequency and the damping to the viscosity and density of the downhole fluid by at least one of: theoretical equations relating frequency and damping to fluid viscosity and density, empirical relationships based on curve fitting to calibration measurements of frequency and damping in fluids of known viscosity and density.

According to a further point, a method for determining the PVT characteristics or phase diagram of a downhole fluid is provided.

According to another point, a method for determining properties of a fluid is provided, that includes the steps of
  a. exposing an electromechanical resonator in an oscillator circuit to an uncharacterized fluid, the oscillator circuit comprising:
    i. an amplifier having an output and an input;
    ii. a feedback loop between the output and input of the amplifier or logic gate; and
    iii. the electromechanical resonator disposed within the feedback loop such that the resonant frequency of the resonator defines the oscillation of the oscillator circuit;
  b. activating the oscillator circuit such that the resonator reaches its resonant frequency in the uncharacterized fluid;
  c. determining the damping of the resonator in the uncharacterized fluid when the oscillator circuit is not activated; and
  d. calculating at least one property of the uncharacterized fluid by reference to the damping.

According to a further point, the uncharacterized fluid is located downhole, and further includes the step of disposing the oscillator circuit downhole.

According to a further point, the tuning fork is disposed in series with the feedback loop.

According to a further point, a method for determining the flow rates for each phase in a multiphase flow is provided.

According to a further point, a viscosity of the fluid is determined by exposing the tuning fork to fluid at a depth of a reservoir prior to the fluid being brought to the surface.

According to a further point, the oscillator circuit is supported by a wireline tool capable of making measurements at multiple points in a well.

According to a further point, the oscillator circuit is supported by untethered sensor platform capable of making measurements at multiple points in a well.

According to a further point, the oscillator circuit is supported by a battery and placed in the wellbore permanently.

According to a further point, the method includes the step of determining a composition of the fluid, wherein the fluid is a multiphase flow.

The subject matter described above is provided by way of illustration only and should not be construed as limiting. Various modifications and changes can be made to the subject matter described herein without following the example embodiments and applications illustrated and described (including, for example, specific circuit values illustrated in the accompanying figures), and without departing from the true spirit and scope of the present invention.

The invention claimed is:

1. A method for determining properties of a downhole fluid, comprising the steps of:
  a) exposing an electromechanical resonator which is part of an oscillator circuit to an uncharacterized downhole fluid, the electromechanical resonator having driving and sensing functions, and the oscillator circuit comprising:
    i) an amplifier having an output and an input;
    ii) a feedback loop between the output and input of the amplifier; and
    iii) the electromechanical resonator disposed within the feedback loop such that a resonant frequency of the electromechanical resonator defines the oscillation frequency of the oscillator circuit, wherein the oscillator circuit comprises a closed loop circuit;

b) activating the oscillator circuit such that the electromechanical resonator reaches the resonant frequency in the uncharacterized fluid;

c) measuring the period of the oscillation of the electromechanical resonator;

d) determining an energy loss parameter of the electromechanical resonator in the uncharacterized fluid; and e) calculating at least one property of the uncharacterized fluid by reference to the energy loss parameter and the period of the oscillator circuit, wherein a parasitic capacitance of the electromechanical resonator is cancelled by using a reference capacitor and a signal subtraction circuit and wherein a constant oscillation amplitude of the oscillator circuit is maintained via an automatic gain adjustment circuitry or a negative resistance control system.

2. The method of claim 1 wherein the electromechanical resonator geometry is one of: a cantilever, a tuning fork, a vibrating wire, and an oscillating plate.

3. The method of claim 1 wherein the electromechanical resonator is actuated into at least one vibrational mode selected from: in-plane, out-of-plane, torsional, scissoring, pivoting, and higher order mode.

4. The method of claim 1, wherein the driving and sensing functions are decoupled.

5. The method of claim 4, wherein the driving and sensing functions are decoupled by relying on different physical effects selected from: electrical, magnetic, mechanical and optical domains.

6. The method of claim 4, wherein the driving and sensing functions are decoupled by physical separation of the driving and sensing locations.

7. The method of claim 1, wherein the uncharacterized fluid is located downhole, and further comprising the step of disposing the oscillator circuit downhole.

8. The method of claim 1, further comprising the step of determining flow rates for each phase in a multiphase flow.

9. The method of claim 1, wherein a viscosity of the fluid is determined by exposing the electromechanical resonator to fluid at a depth within a well before the fluid is brought to a surface.

10. The method of claim 1, wherein the electromechanical resonator is housed in a chamber and a portion of the uncharacterized downhole fluid is selectively drawn into the chamber and separated and/or conditioned, chemically or physically, to perform the measuring step.

11. The method of claim 1, wherein the uncharacterized downhole fluid comprises at least one of a fluid, dispersed fluid-fluid, solid-fluid, or gas-fluid system and wherein properties of a phase diagram of the uncharacterized downhole fluid are inferred from viscosity and density changes and their dependence on pressure, temperature, volume, or concentration of a dispersed phase.

12. The method of claim 1, wherein the electromechanical resonator is selectively coated to change its affinity to the uncharacterized downhole fluid or a chemical.

13. The method of claim 1, wherein the oscillator circuit is supported by a wireline tool capable of making measurements at multiple points in a well.

14. The method of claim 1, wherein the oscillator circuit is supported by an untethered sensor platform capable of making measurements at multiple points in a well.

15. The method of claim 1, further comprising the step of determining a composition of the fluid, wherein the fluid is a multiphase flow.

16. An apparatus for determining properties of an uncharacterized downhole fluid, comprising:

a) an oscillator circuit comprising an amplifier having an output and an input, a feedback loop between the output and input of the amplifier or a logic gate, and an electromechanical resonator disposed within the feedback loop such that a resonant frequency of the resonator defines an oscillation frequency of the oscillator circuit, wherein the oscillator circuit comprises a closed loop circuit;

b) means for causing the oscillator circuit to stop driving the resonator, which thereby enables observation of a decay rate of the oscillation within the uncharacterized fluid;

c) means for measuring the decay rate of the oscillation; and d) means for calculating at least one property of the uncharacterized fluid by reference to a damping comprising the measured decay rate, wherein a parasitic capacitance of the electromechanical resonator is cancelled by using a reference capacitor and a signal subtraction circuit and wherein a constant oscillation amplitude of the oscillator circuit is maintained via an automatic gain adjustment circuitry or a negative resistance control system.

* * * * *